United States Patent [19]

Davis

[11]  4,432,977
[45]  Feb. 21, 1984

[54] METHOD FOR DILATING THE SMOOTH MUSCLES OF THE UPPER URINARY TRACT

[75] Inventor: William M. Davis, Tucson, Ariz.

[73] Assignee: William P. Poythress & Company, Tucson, Ariz.

[21] Appl. No.: 412,238

[22] Filed: Aug. 27, 1982

[51] Int. Cl.³ .................... A61K 27/00; A61K 31/24; A61K 31/135; A61K 31/445

[52] U.S. Cl. ................... 424/248.5; 424/207; 424/309; 424/330

[58] Field of Search .................... 424/330, 248.5, 267, 424/309

Primary Examiner—Stanley J. Friedman
Attorney, Agent, or Firm—Austin R. Miller

[57] ABSTRACT

Dilation of smooth muscles of the upper urinary tract with a di-N-substituted aminoethyl ester of diphenylthioacetic acid.

12 Claims, No Drawings

METHOD FOR DILATING THE SMOOTH MUSCLES OF THE UPPER URINARY TRACT

BACKGROUND OF THE INVENTION

1. Field of the Invention

This invention relates to a novel method of dilating the smooth muscles of the upper urinary tract. Such an invention has many novel applications including but not limited to the treatment of patients passing kidney stones through the upper urinary tract.

2. Description of the Prior Art

To date, no clinically effective upper urinary tract dilator is in use. Currently used urinary tract dilators are generally anti-cholinergic drugs or direct smooth muscle relaxants such as papavarin, a narcotic derivative. These drugs have either been ineffective as dilators or have undesirable side effects such as dryness of the mouth, blurred vision, and slowed heart beat.

Thiphenamil hydrochloride is a class of compounds comprising a di-N-substituted aminoethyl ester of diphenylthioacetic acid having the formula:

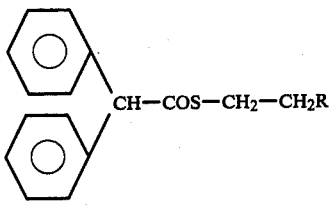

in which R represents a disubstituted amino radical of either the diethylamino group, the morpholino group or the piperidino group.

The prior uses for thiphenamil hydrochloride center around its use as an anti-spasmotic agent in the upper and lower gastro-intestinal tract for pylorospasm, spasm associated with the gallbladder and common bile duct, as well as diarrhea and the irritable bowel syndrome. Prior art uses also include treatment of ureterospasm and bladder irritation.

There have been further reports that thiphenamil hydrochloride has been successfully used for the treatment of bronchospasm.

Thiphenamil hydrochloride is a well-known compound and is described in detail in U.S. Pat. No. 2,390,555 to Richardson, incorporated herein by reference. Additional methods of making thiphenamil hydrochloride are described in U.S. Pat. No. 2,510,773 to Clinton.

Thus, it is an important object of the present invention to provide a method for dilating and relaxing the smooth muscles of the upper urinary tract without subjecting the patient to the undesirable side effects of anti-cholinergic drugs, for example dryness of the mouth, dilation of the pupils, and slowed heart beat.

It is a further important object of the present invention to provide such a method which is safe for use on human patients and which is also safe for particularly sensitive patients such as glaucoma patients.

It is yet another object of the present invention to provide a method for treating patients passing kidney stones without subjecting the patient to surgery.

It is another important object of the present invention to provide such a method of dilating and relaxing the smooth muscles of the upper urinary tract without leaving or accumulating any foreign substances in the human body tissues.

SUMMARY OF THE INVENTION

These and other objects are met in the novel method for dilating the smooth muscles of the upper urinary tract comprising the administration of a di-N-substituted aminoethyl ester of diphenylthioacetic acid having the formula:

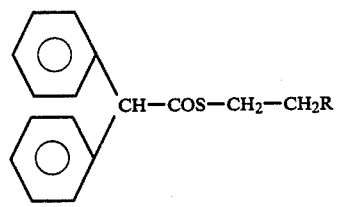

in which R represents a disubstituted amino radical of the group consisting of the diethylamino group, the morpholino group and the piperidino group.

A more specific method for treating a patient passing a kidney stone comprises administering to the patient a di-N-substituted aminoethyl ester of diphenylthioacetic acid of the formula:

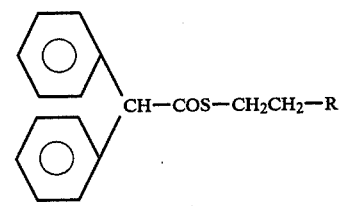

in which R represents a disubstituted amino radical of the group consisting of the diethylamino group, the morpholino group and the piperidino group.

DESCRIPTION OF THE PREFERRED EMBODIMENTS

It is now been surprisingly discovered that thiphenamil hydrochloride can be used for dilating the smooth muscles of the upper urinary tract and specifically to dilate and relax the smooth muscles of the upper urinary tract in order to treat a patient passing a kidney stone through the upper urinary tract.

It is evident from the experimental results which follow that thiphenamil hydrochloride increases the compliance of the renal pelvis. Under conditions of increased compliance, the capacity of the renal pelvis is significantly increased. Additionally, the renal pelvic pressure is concomitantly reduced with the contractile rate. Under these circumstances, the upper urinary tract dilates and peristaltic contractions are greatly diminished in both amplitude and frequency.

Further, thiphenamil hydrochloride acts as an effective upper urinary tract dilator and would be effective in treating patients passing kidney stones through the upper urinary tract.

The experimental results reveal that thiphenamil hydrochloride acts as an effective upper urinary tract dialator in a dosage range of from about 0.7 to about 11.4 mg per kilogram of body weight. A preferred dosage is in the range of from about 1.4 to about 5.7 mg per kiligram of body weight. A still more preferred dosage range is from about 2.8 to about 5.7 mg per kilogram of body weight.

Thiphenamil hydrochloride can be administered orally, typically in tablets of 100–400 mg, or by intravenous injection.

Because thiphenamil hydrochloride slowly hydrolyzes in water, it is generally not used as a serum or suspension. It is possible however to encapsulate microspheres of thiphenamil hydrochloride in the form of a liquid suspension for administration to patients.

The invention is further disclosed by means of the following examples which are intended only as illustrations and which in no way limit the invention.

EXAMPLES 1–9

Nine pigs, five male and four female, were implanted with a telemetry package to record the amplitude and frequency of the filling and emptying phase of the renal pelvis. The pigs were lightly anesthetized with 2% halothane and 98%, oxygen. A dose of 1 milligram of a thiphenamil hydrochloride (in which R is a disubstituted amino radical of the diethylamino group) per kilogram of body weight (mg/kg) was given to each pig intravenously through an ear vein following a 20 minute control period.

EXAMPLES 10–18

The same procedures as followed in examples 1–9 were repeated using a dose of 1 milligram of a thiphenamil hydrochloride (in which R is a disubstituted amino radical of the morpholino group) per kilogram of body weight (mg/kg).

EXAMPLES 19–27

The same procedures as followed in examples 1–18 were repeated using a dose of 1 milligram of a thiphenamil hydrochloride (in which R is a disubstituted amino radical of the piperidino group) per kilogram of body weight (mg/kg).

Examples 1–27 demonstrate that at a dose of 1 mg/kg thiphenamil hydrochloride (all types) the rate of contraction in the renal pelvis increases from $1.84 \pm 0.15$ to $2.03 \pm 0.35$ contractions per minute.

EXAMPLES 28–54

The same procedure as utilized in examples 1–27 was used on the nine pigs which were given a dose of 2 milligrams of: first, a thiphenamil hydrochloride (in which R is a disubstituted amino radical of the diethylamino group) per kilogram of body weight; second, a 2 milligram dose of a thiphenamil hydrochloride (in which R is a disubstituted amino radical of the morpholino group) per kilogram of body weight (mg/kg); and third, a 2 milligram dose of a thiphenamil hydrochloride (in which R is a disubstituted amino radical of the piperidino group) per kilogram of body weight (mg/kg).

EXAMPLES 55–81

The same procedure as utilized in examples 1–54 was used on the nine pigs which were given a dose of 5 milligrams of: first, a thiphenamil hydrochloride (in which R is a disubstituted amino radical of the diethyl amino group) per kilogram of body weight (mg/kg); second, a 5 milligram dose of a thiphenamil hydrochloride (in which R is a disubstituted amino radical of the morpholino group) per kilogram of body weight (mg/kg); and third, a 5 milligram dose of a thiphenamil hydrochloride (in which R is a disubstituted amino radical of the piperidino group) per kiligram of body weight (mg/kg).

EXAMPLES 82–108

The same procedure as utilized in examples 1–80 was used on the nine pigs which were given a dose of 10 milligrams of: first, a thiphenamil hydrochloride (in which R is a disubstituted amino radical of the diethylamino group) per kilogram of body weight (mg/kg); second, a 10 milligram dose of a thiphenamil hydrochloride (in which R is a disubstituted amino radical of the morpholino group) per kilogram of body weight (mg/kg); and third, a 10 milligram dose of a thiphenamil hydrochloride (in which R is a disubstituted amino radical of the piperidino group) per kiligram of body weight (mg/kg).

The in vivo data show that the effect of thiphenamil hydrochloride on renal pelvic frequency is bimodal. Thus, while at a dose of 1 mg/kg of thiphenamil hydrochloride (all types) the renal pelvis contraction frequency increases, at doses greater than 1 mg/kg of thiphenamil hydrochloride (all types) the frequency of pelvic contractions decreases significantly. The data follows a roughly linear equation computed from the dose response curves:

$$\Delta F = -11.5 - 3.3X$$

where $\Delta F$ is the percent change in frequency and X is the dose of thiphenamil hydrochloride in miligrams per kiligram of body weight.

In the test animals, renal pelvic pressure decreased significantly from a mean of $6.6 \pm 0.66$ cm $H_2O$ to $2.3 \pm 0.16$ cm $H_2O$.

In five of the experimental animals, measurements were taken with the abdomen open and the ureter obstructed. Under these circumstances renal pelvic pressure was effectively raised to a mean value of $18.4 \pm 6.3$ cm of $H_2O$. Intravenous thiphenamil hydrochloride at 2.5 mg/kg significantly reduced the resting renal pelvic pressure to $5.9 \pm 3.1$ cm $H_2O$ in four of the five test animals.

The data also demonstrate a linear decrease in the frequency of spontaneous renal pelvic contractions. A linear equation computed from the dose response curves is given by:

$$\Delta F = -5.2 - 5.6X$$

where $\Delta F$ is the percent change in frequency and X is the dose of thiphenamil hydrochloride in $10-3$ M. Furthermore, the amplitude of the spontaneous contractions decreased according to the relationship:

$$\Delta T = 1.2 + 0.4X$$

where $\Delta T$ is the percentage decrease in amplitude of contraction and X is the dose of thiphenamil hydrochloride at $10-3$ M.

Experiments 1–108 show that at doses above 1 mg/kg, thiphenamil hydrochloride will act as an effective agent to dilate and relax the upper urinary tract smooth muscles and further suggest that thiphenamil hydrochloride (all types) will be effective in treating patients passing kidney stones.

I claim:

1. A method for dilating the smooth muscles of the upper urinary tract comprising administering to a patient requiring such treatment an effective amount of a di-N-substituted aminoethyl ester of diphenylthioacetic acid having the formula:

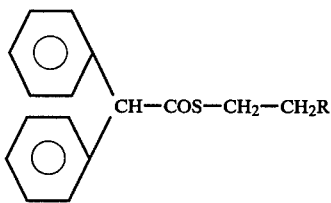

in which R represents a disubstituted amino radical of the group consisting of the diethylamino group, the morpholino group and the piperidino group.

2. The method as described in claim 1, wherein the di-N-substituted aminoethyl ester of diphenylthioacetic acid is administered in a dosage of from about 0.7 to about 11.4 mg per kiligram of body weight.

3. The method as described in claim 1, wherein the di-N-substituted aminoethyl ester of diphenylthioacetic acid is administered in a preferred dosage of from about 1.4 to about 5.7 mg per kiligram of body weight.

4. The method as described in claim 1, wherein the di-N-substituted aminoethyl ester of diphenylthioacetic acid is administered in a more preferred dosage of from about 2.8 to about 5.7 mg per kiligram of body weight.

5. The method as described in claim 2, wherein the di-N-substituted aminoethyl ester of diphenylthioacetic acid is combined with a pharmaceutically accepted carrier.

6. A method of treating a patient passing a kidney stone comprising administering to the patient an effective amount of a di-N-substituted aminoethyl ester of diphenylthioacetic acid of the formula:

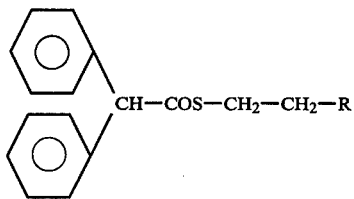

in which R represents a disubstituted amino radical of the group consisting of the diethylamino group, the morpholino group and the piperidino group.

7. The method as described in claim 6, wherein the di-N-substituted aminoethyl ester of diphenyl-thioacetic acid is administered in a dosage in the range from about 0.7 to about 11.4 mg per kiligram of body weight.

8. The method as described in claim 6, wherein the di-N-substituted aminoethyl ester of diphenylthioacetic acid is administered in a preferred dosage in the range from about 1.4 to about 5.7 mg per kilogram of body weight.

9. The method as described in claim 6, wherein the di-N-substituted aminoethyl ester of diphenylthioacetic acid is administered in a more preferred dosage in the range from about 2.8 to about 5.7 mg per kiligram of body weight.

10. The method as described in claim 7, wherein the di-N-substituted aminoethyl ester of diphenylthioacetic acid is combined with a pharmaceutically acceptable carrier.

11. A method for dilating the smooth muscles of the upper urinary tract comprising directly effecting the muscle fibers and the pacemaker of contractility of the renal pelvis and ureter to allow the passage of an obstructing, intraluminal foreign body, by administering to a patient requiring such treatment a di-N-substituted aminoethyl ester of diphenylthioacetic acid having the formula:

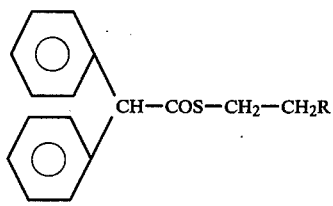

in which R represents a disubstituted amino radical of the group consisting of the diethylamino group, the morpholino group and the piperidino group.

12. A method of treating a patient having an upper urinary tract which is at least partially obstructed by a renal calculus comprising altering the renal pelvis and ureteral contractile pacemaker to allow ureteral dilitation and calculus passage by administering to the patient a di-N-substituted aminoethyl ester of diphenylthioacetic acid of the formula:

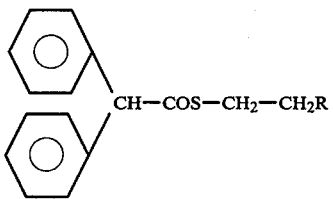

in which R represents a disubstituted amino radical of the group consisting of the diethylamino group, the morpholino group and the piperidino group.

* * * * *